(12) United States Patent  (10) Patent No.: US 8,209,810 B2
Samuel  (45) Date of Patent: Jul. 3, 2012

(54) CLEANING APPARATUS

(75) Inventor: Peter Samuel, Dalkeith Lodge (GB)

(73) Assignee: City Hospitals Sunderland NHS Trust (GB)

( * ) Notice: Subject to any disclaimer, the term of this patent is extended or adjusted under 35 U.S.C. 154(b) by 758 days.

(21) Appl. No.: 12/161,972

(22) PCT Filed: Jan. 26, 2007

(86) PCT No.: PCT/GB2007/050041
§ 371 (c)(1),
(2), (4) Date: Aug. 30, 2008

(87) PCT Pub. No.: WO2007/085877
PCT Pub. Date: Aug. 2, 2007

(65) Prior Publication Data
US 2009/0025161 A1   Jan. 29, 2009

(30) Foreign Application Priority Data
Jan. 26, 2006   (GB) .................................. 0601565.5

(51) Int. Cl.
*B08B 1/04*   (2006.01)

(52) U.S. Cl. ....... 15/104.2; 15/106; 15/160; 15/104.061

(58) Field of Classification Search ........... 15/24, 104.2, 15/104.061, 106, 160, 25, 104.18, 104.33, 15/104.11, 104.12, 104.3; 600/569, 510
See application file for complete search history.

(56) References Cited

U.S. PATENT DOCUMENTS

| 2,739,585 | A | * | 3/1956 | Ayre | 600/569 |
| 2,847,990 | A | | 8/1958 | Ayre | |
| 6,093,155 | A | * | 7/2000 | Ouchi | 600/569 |
| 2002/0056219 | A1 | | 5/2002 | Solberg et al. | |
| 2002/0108195 | A1 | | 8/2002 | Seder et al. | |
| 2003/0109837 | A1 | | 6/2003 | McBride-Sakal | |

FOREIGN PATENT DOCUMENTS

DE   20 2004 000377  U1   6/2004

* cited by examiner

*Primary Examiner* — Dung V Nguyen
(74) *Attorney, Agent, or Firm* — MacMillan, Sobanski & Todd, LLC

(57) ABSTRACT

Tracheo-oesophageal valve cleaning apparatus comprises a fluid dispenser with a fluid reservoir and an outlet; a cleaning element mounted proximal to the outlet; and a drive mechanism including an element mounted axially within the said fluid dispenser, wherein axial movement of the element of the drive mechanism towards to the outlet causes both rotation of cleaning element and fluid to be dispensed from the outlet.

19 Claims, 8 Drawing Sheets

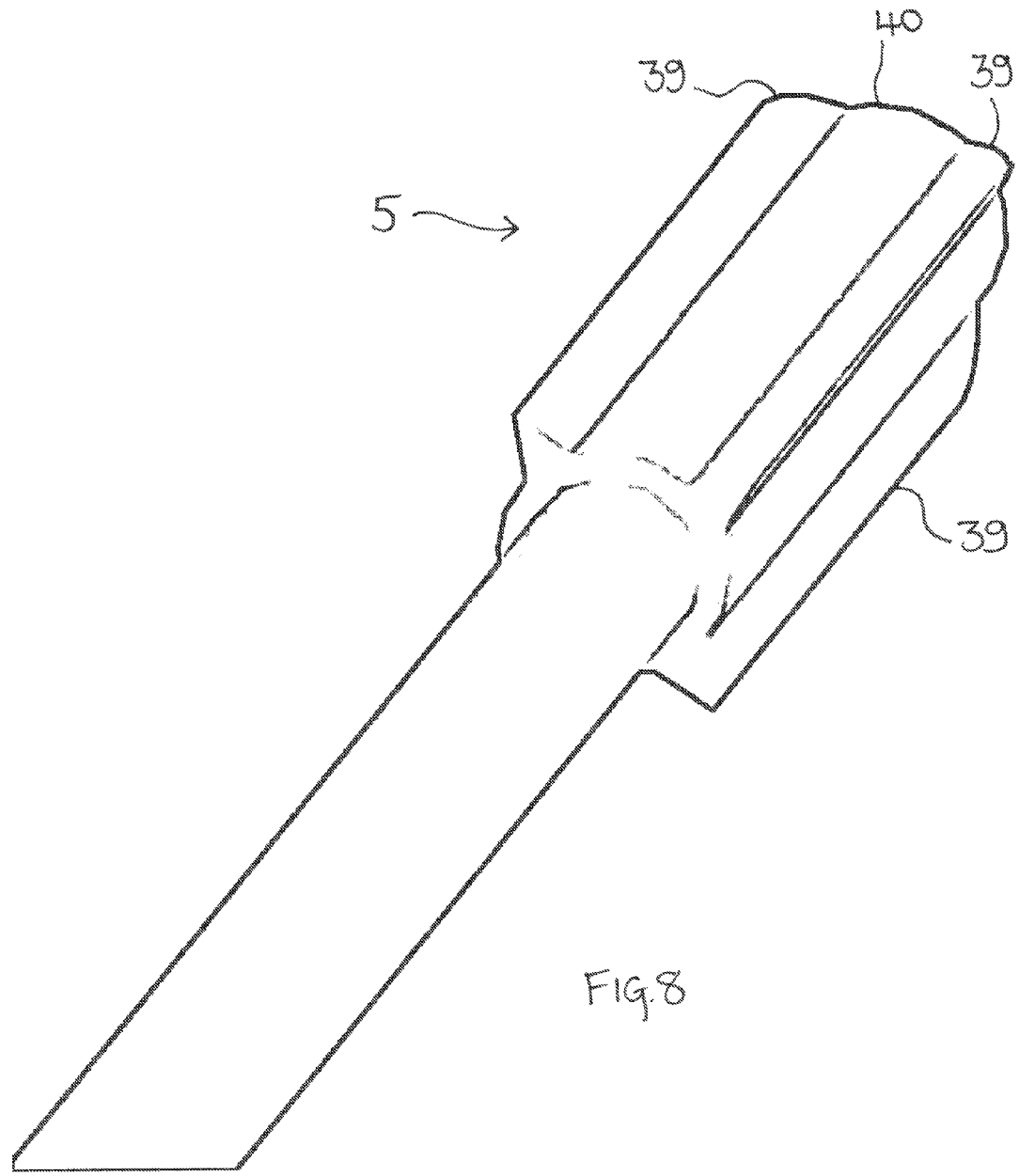

CLEANING APPARATUS

FIELD OF THE INVENTION

The invention relates to cleaning apparatus; in particular to apparatus for cleaning tracheo-oesophageal valves.

BACKGROUND OF THE INVENTION

A laryngectomy is a surgical procedure which involves the removal of a patient's voice box and other surrounding structures often for treatment of cancer of the larynx.

Tracheo-oesophageal prosthetic valves are devices which allow vocal function to be restored to a patient following a laryngectomy. This type of valve is inserted into a hole between the trachea and the oesophagus. The valve blocks the flow of secretions and food materials from the oesophagus to the airway, but allows a passage of air from the airway into the throat to permit speech.

These valves usually stay in place for approximately 6 months before being replaced by a doctor or nurse or other specially trained therapist. The valves can easily become contaminated with secretions and yeasts from the mouth which can cause infections. This can stop the device working altogether, necessitating the replacement of the valve. To prevent this happening, the valves must be cleaned daily by the patient. If valves are not cleaned effectively then their life span is shortened. Frequent replacement of these indwelling valves is not only inconvenient for a patient but can cause trauma to the opening in which the device is placed. These valves are also expensive and frequent replacement causes unnecessary expense.

Cleaning products available currently include small brushes for insertion into the valve, and pipettes with which to flush liquid through the valve. The pipettes available on the market do not give a good seal against the valve and leakage occurs during use which is inconvenient to the user. Also, the pipettes cannot be used at the same time as using a brush.

US 2002/0056219 describes a device for cleaning the inside of a gun barrel. The cleaner comprises a brush attached to a hollow rod with a handle at the opposite end. The brush is mounted so it can freely rotate when the handle is held stationary. A squeeze bottle containing cleaning fluid at the handle end can be squeezed to allow cleaning fluid to run along the hollow rod and onto the brush.

Brushes and pipettes available for cleaning these valves do not give very effective cleaning. The device described in US 2002/0056219 would not be suitable for cleaning tracheo-oesophageal valves as using this type of device would require the user to manually manipulate and rotate the brush whilst squeezing the bottle to dispense fluid into the valve.

The present invention offers cleaning apparatus that mitigates the above-identified problems.

SUMMARY OF THE INVENTION

The invention provides tracheo-oesophageal valve cleaning apparatus as specified in Claim 1.

Preferred aspects of the invention are specified in the claims dependent on Claim 1.

The invention provides apparatus that offers more effective cleaning of indwelling tracheo-oesophageal valves. The apparatus of the invention provides a combined brush and fluid dispenser that dispenses an amount of fluid in a one action flush, the brush being rotated to clean the valve by the same action that forces fluid across the brush and into the valve. More effective cleaning leads to prolonged life of the valves.

BRIEF DESCRIPTION OF THE DRAWINGS

In the drawings, which illustrate preferred embodiments of the invention:

FIG. 8 shows an embodiment of the cleaning element of the cleaning apparatus of FIGS. 1 and 5.

DETAILED DESCRIPTION OF THE PREFERRED EMBODIMENTS

Figure 1:
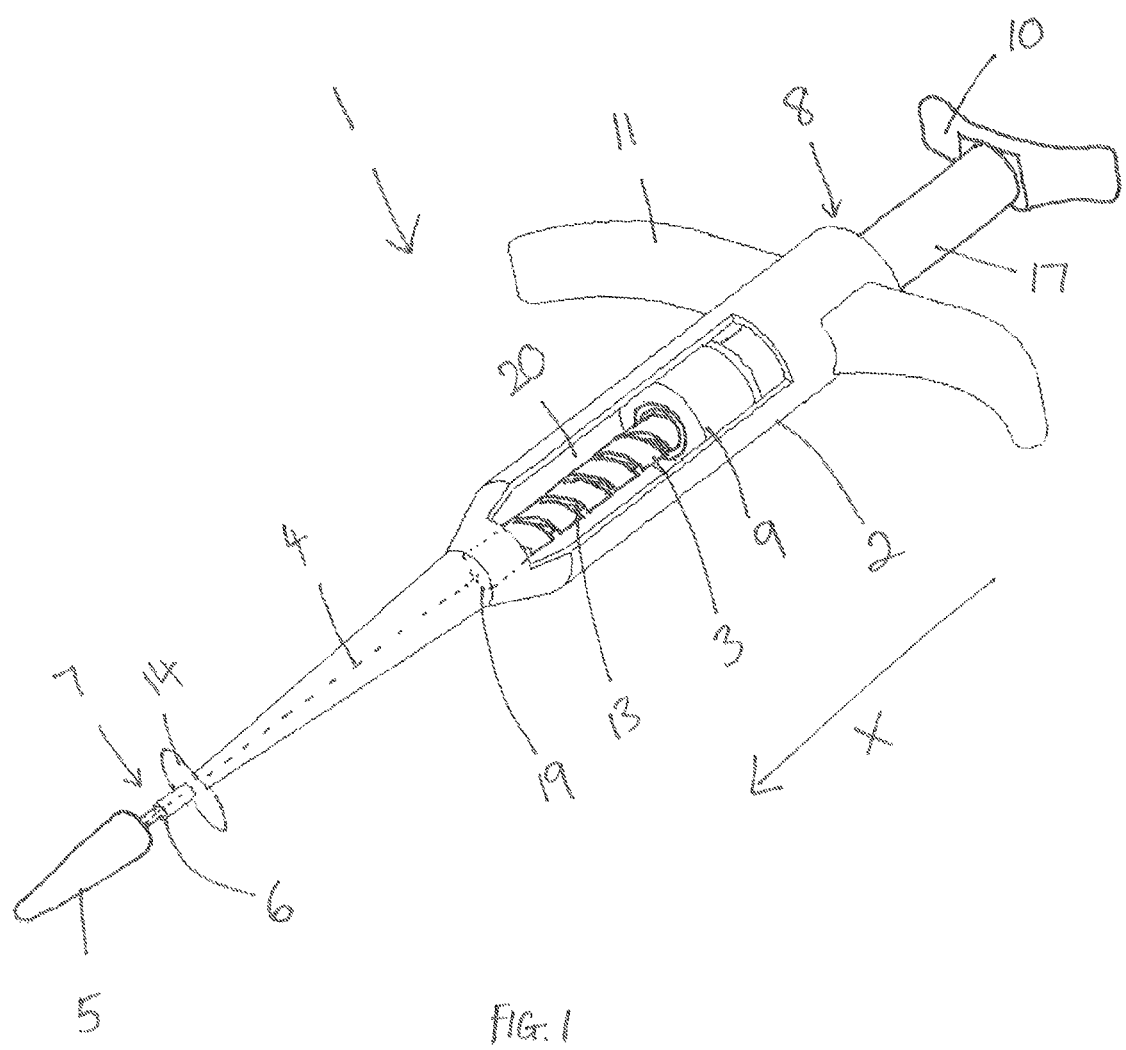
FIG. 1 shows a first embodiment of a cleaning apparatus in a 'before use' configuration.

With reference to FIG. 1, a first embodiment of a cleaning apparatus 1 comprises a fluid dispenser 2 with a first narrow end 7 and a second broader end 8. A rod 3 is present within the fluid dispenser 2. The rod 3 is connected to a shaft 4 which extends beyond the fluid dispenser 2 and out through an outlet 6. The shaft 4 is connected to a cleaning element, which in the example is a brush 5.

The brush 5 may be detachable from the tip of the shaft 4. The shaft 4 may also be removable from the end 19 of the rod 3. Alternatively, both the brush 5 and shaft 4 may together be detachable from the end 19 of the rod 3. The brush 5 and shaft 4 or the brush 5 may therefore be removed and replaced as necessary, without the need to replace the cleaning apparatus 1.

The fluid dispenser 2 includes a cylindrical fluid reservoir 20. A hollow plunger 17 fits into the cylinder 20. A seal 9 between the plunger 17 and the cylinder 20 prevents fluid from leaking at broad end 8 of the fluid dispenser 2. The plunger 17 mounts the seal 21 at one end thereof and a handle 10 at the other end. The rod 3 is located within plunger 17. The end of the hollow plunger 17 mounting the handle 10 is sealed, whereas the end mounting the seal 9 includes an opening. The rod 3 is located within the plunger 17.

The fluid reservoir 20 is filled with cleaning fluid for ejection from the outlet 6. In a preferred embodiment the cleaning fluid is a saline solution or sodium bicarbonate. The reservoir 20 may be pre-filled with cleaning fluid, and the outlet 6 may be provided with a seal to prevent leakage of fluid before use of the apparatus 1. Alternatively, the user may fill the reservoir 20 with cleaning fluid immediately prior to use.

Figure 2:
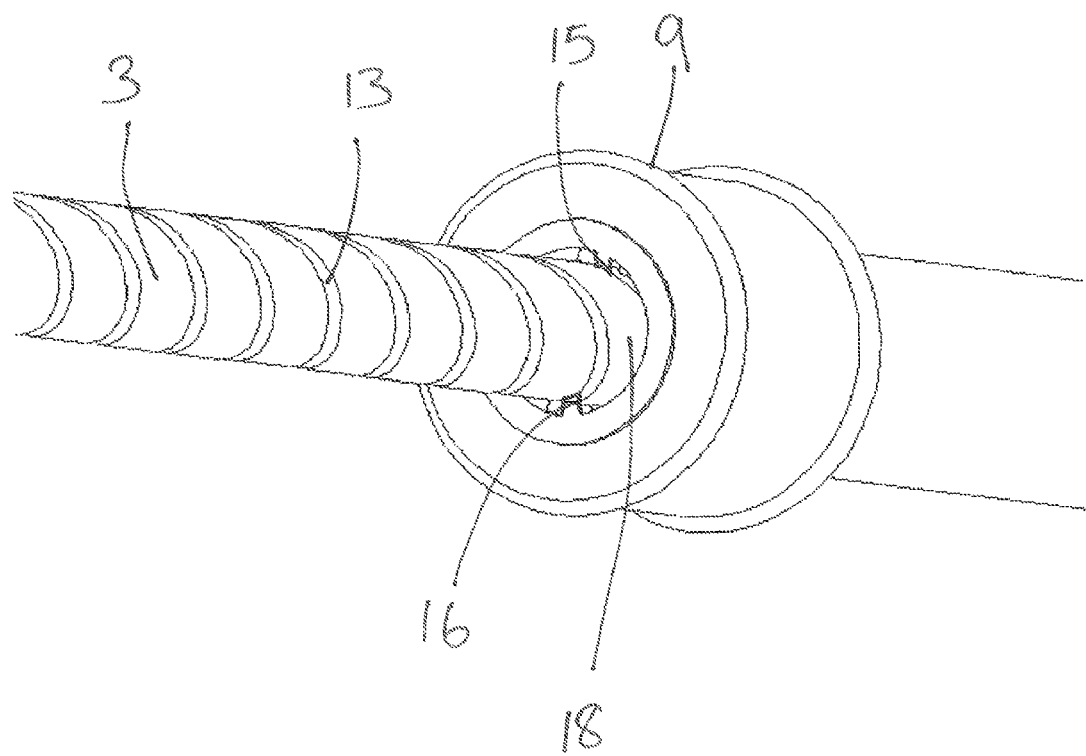
FIG. 2 is an exploded view of the internal workings of the apparatus of FIG. 1.

As shown in FIG. 2, the rod 3 is generally cylindrical in shape and has a substantially helical groove 13 extending along its outer surface.

The end 18 of the rod 3 is mounted within the plunger 17 such that it can freely rotate about its longitudinal axis. The other end 19 of the rod 3 sits in a housing formed in the dispenser 2 such that the rod 3 can freely rotate about its longitudinal axis but is constrained against movement in the direction X. The plunger 17 includes two protruding elements 15 and 16 each extending into groove 13 of the rod 3.

Figure 3:
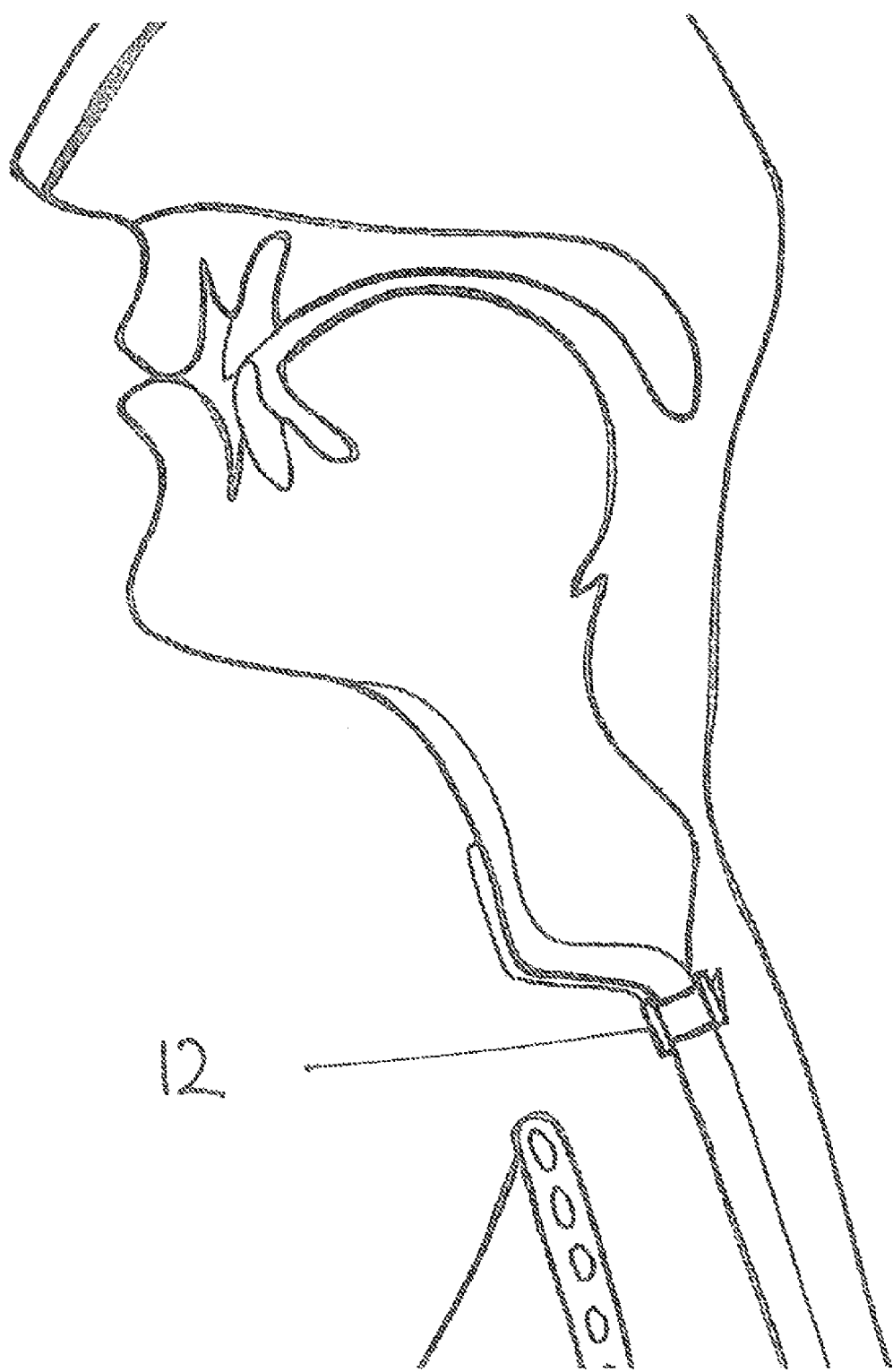
FIG. 3 show the location of a tracheo-oesophageal valve.
Figure 4:
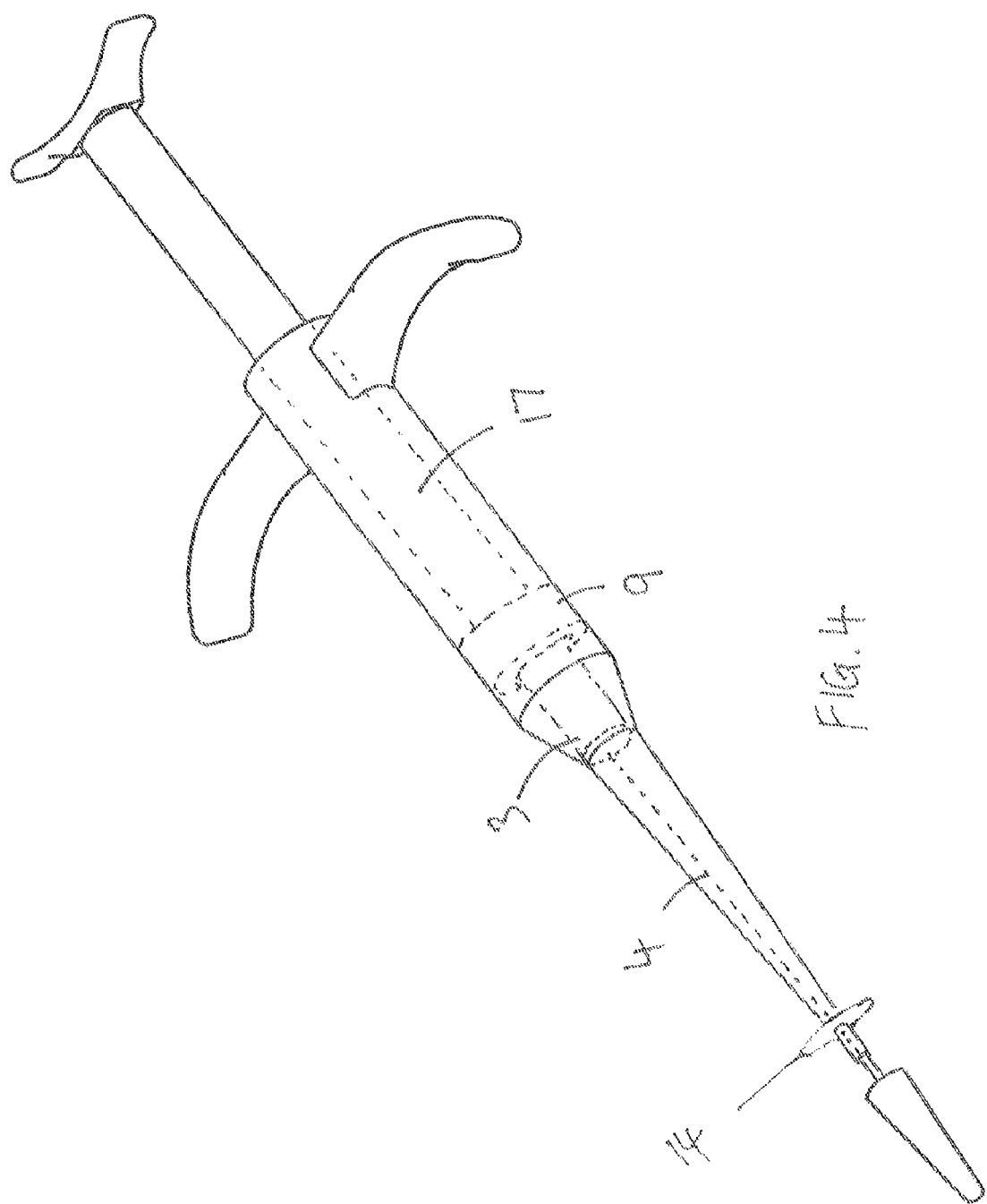
FIG. 4 shows the cleaning apparatus of FIG. 1 after use.

In use, the user inserts the brush 5 into the tracheo-oesophageal valve 12 (FIG. 3). A lip 14 of larger diameter than the brush 5 may be present. The lip 14 prevents the user inserting the dispenser 2 too far into valve 12. Inserting a brush too far into the valve could damage the valve and a replacement may be required. The user grasps the device using the handles 11 and depresses the plunger 17 using the handle 10, applying pressure in the direction labelled X in FIG. 1. The movement of the rod 3 is constrained against movement in direction X as the end 19 of the rod 3 is in contact with the walls of the dispenser 2. The protrusions 15 and 16 are forced to move along the helical groove 13 and the rod 3 is forced to rotate, thereby rotating the brush 5 inside the valve 12. As the rod 3 rotates, the plunger 17 moves axially inside the dispenser 2 in the direction X. This axial movement of the plunger 17 forces fluid to flow out through the outlet 6, over the brush 5, and into the valve 12. FIG. 4 shows the position of the plunger 17 after use.

The fluid dispenser 2 may be refilled with fluid after each use by placing the outlet 6 into an amount of fluid. Fluid is drawn up into the fluid reservoir 20 of the dispenser 2 by withdrawing the piston 17 to its original position (see FIG. 1). The rod 3 is constrained against movement in direction X as it is rotatably connected with the walls of the dispenser 2. For example the walls of the dispenser 2 may comprise a groove in which sits one or more protrusions extending radially from the rod 3. The protrusions 15 and 16 are forced to move back along the helical groove 13. As the plunger 17 is withdrawn, the rod 3 is forced to rotate and the reservoir 20 is re-filled with fluid.

Figure 5:
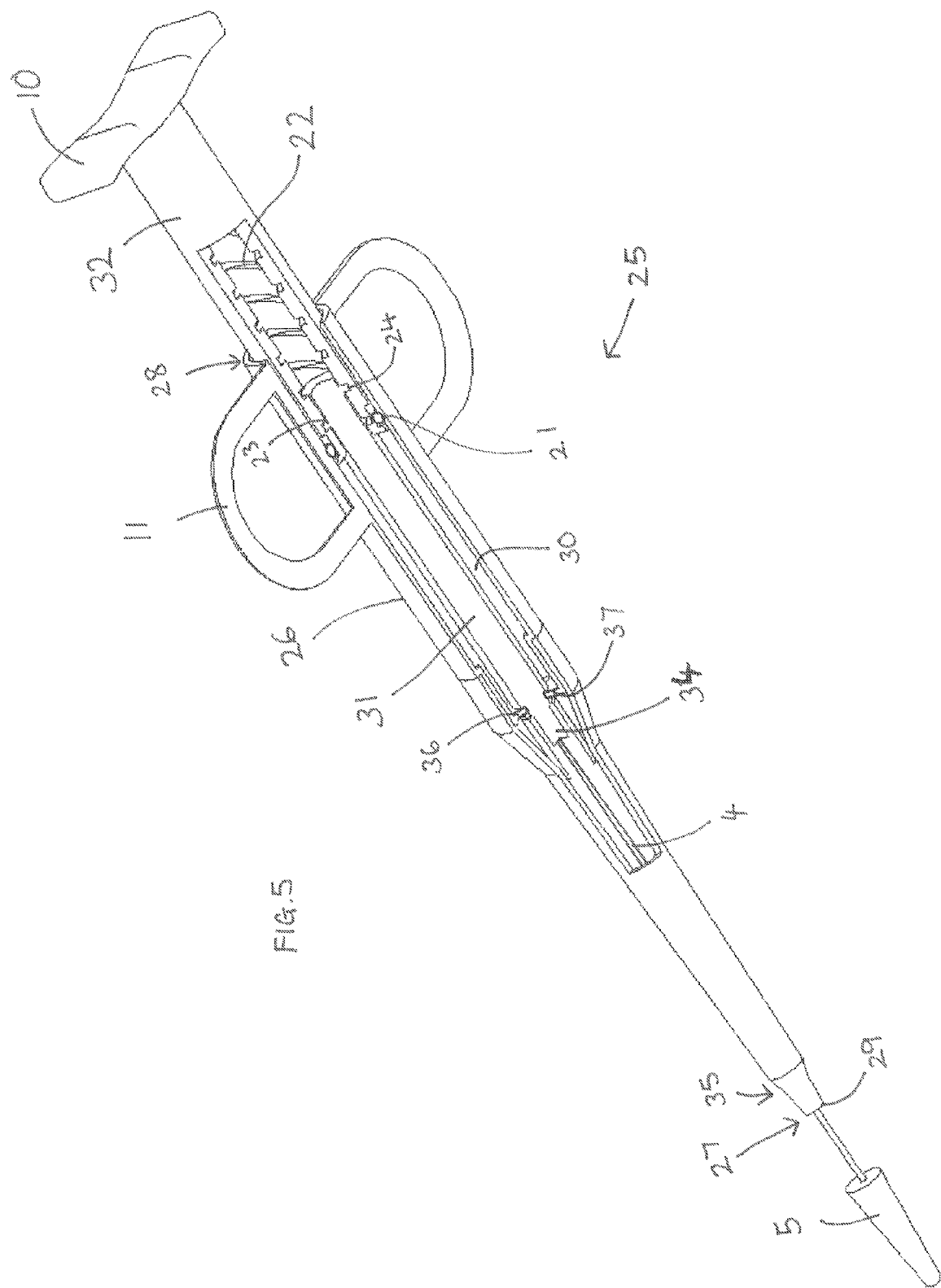
FIG. 5 shows a second embodiment of a cleaning apparatus, with a cutaway portion showing the internal workings of the apparatus.
Figure 6:
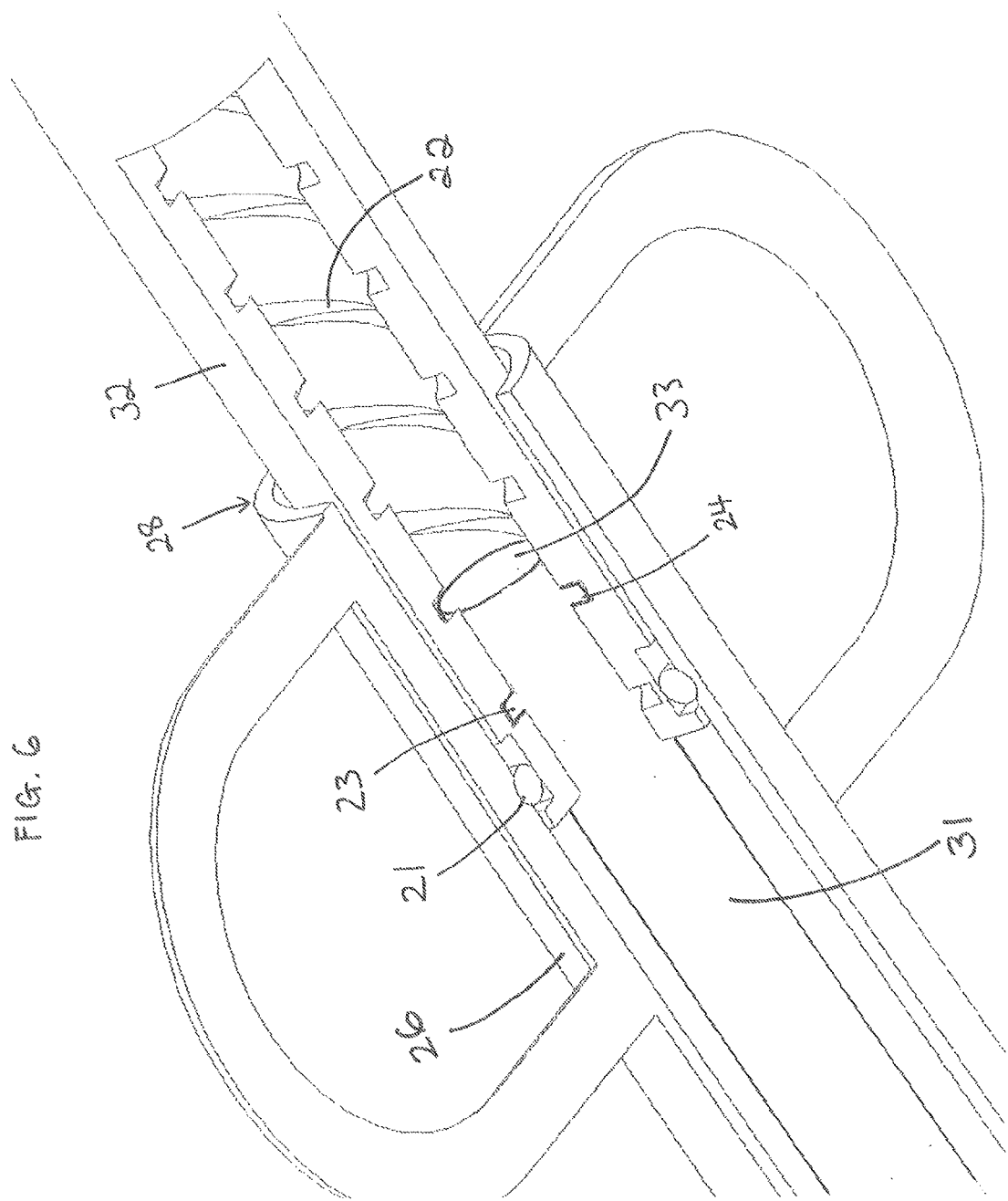
FIG. 6 shows an exploded cross-sectional view of the internal workings of the apparatus of FIG. 5.

FIGS. 5 and 6 illustrate a second embodiment of the invention. Like reference numerals are used to refer to like features.

With reference to FIGS. 5 and 6, a second embodiment of cleaning apparatus 25 comprises a fluid dispenser 26 with a first narrow end 27 and a second broader end 28. A rod 31 is present within the fluid dispenser 26. The rod 31 is connected to a shaft 4 which extends beyond the dispenser 26 and out through an outlet 29. The shaft 4 is connected to a brush 5. As in the previous embodiment, the brush 5 may be detachable from the cleaning apparatus 1. The shaft 4 may also be removable. The brush 5 and shaft 4 together may be detachable from the cleaning apparatus 1.

The fluid dispenser 26 includes a cylindrical fluid reservoir 30. A hollow plunger 32 fits closely into the cylinder 30. A circular seal 21 between the plunger 32 and the cylinder 30 seals the fluid reservoir 30, minimising any leakage of fluid from the broad end 28 of the dispenser 26. The plunger 32 mounts the seal 21 at one end thereof and a handle 10 at the other end. The rod 31 is located within the plunger 32.

The fluid reservoir 30 is filled with cleaning fluid for ejection from outlet 29. In a preferred embodiment the cleaning fluid is a saline solution or a sodium bicarbonate solution. As with the previous embodiment, the reservoir 30 may be pre-filled with cleaning fluid, and the outlet 29 may be provided with a seal to prevent leakage of fluid before use of the apparatus 25. Alternatively, the user may fill the reservoir 30 with cleaning fluid immediately prior to use.

As shown in FIG. 6, the internal hollow of plunger 32 is substantially cylindrical in shape and has a substantially helical groove 22 extending along its inner surface.

The end 33 of the rod 31 is mounted within the plunger 32 such that it can freely rotate about its longitudinal axis. The other end 34 of the rod 31 sits in a housing formed in the dispenser 26 such that the rod 31 can freely rotate about its longitudinal axis but is constrained against movement in the direction X. The rod 31 includes two protruding elements 23 and 24 each extending into the groove 22 on the internal surface of the hollow plunger 32.

In use, the user inserts the brush 5 into their tracheo-oesophageal valve 12 (FIG. 3). The narrow end 27 of the dispenser 26 is tapered. The tapered end 35 prevents the user inserting the dispenser 26 too far into valve 12. The user grasps the device using the handles 11 and depresses the plunger 10, applying pressure in the direction labelled X in FIG. 5. The movement of the rod 31 is constrained against movement in direction X as it is rotatably connected with the walls of the dispenser 26. In this embodiment the rod 31 comprises a circular groove in which sits one or more protrusions 36 and 37 extending radially from the dispenser 26. Protrusions 36 and 37 are forced to move along this circular groove and hence movement of the rod 31 is constrained against movement in the direction X. As the plunger is depressed, the protrusions 23 and 24 are forced to move along the helical groove 22 and the rod 31 is forced to rotate, thereby rotating the brush 5 inside the valve 12. As the rod 31 rotates, the plunger 32 moves axially inside the dispenser 26 in the direction X. This axial movement of the plunger 32 forces fluid to flow out through the outlet 29, over the brush 5, and into the valve 12.

As with the previous embodiment, the fluid dispenser 26 may be refilled with fluid after each use by placing the outlet 29 into an amount of fluid. Fluid is drawn up into the fluid reservoir 30 of the dispenser 26 by withdrawing the plunger 32 to its original position. The rod 31 is constrained against movement in direction X as it is rotatably connected with the walls of the dispenser 26. As fluid is drawn up, the protrusions 23 and 24 on the rod are forced to move back along helical groove 22. As the plunger 32 is withdrawn, the rod 31 is forced to rotate and the reservoir 30 is re-filled with fluid. There may also be a lip at the broader end 28 of the dispenser 26 to prevent the plunger being unintentionally removed from the dispenser 26 when refilling the fluid reservoir 30.

Figure 7:
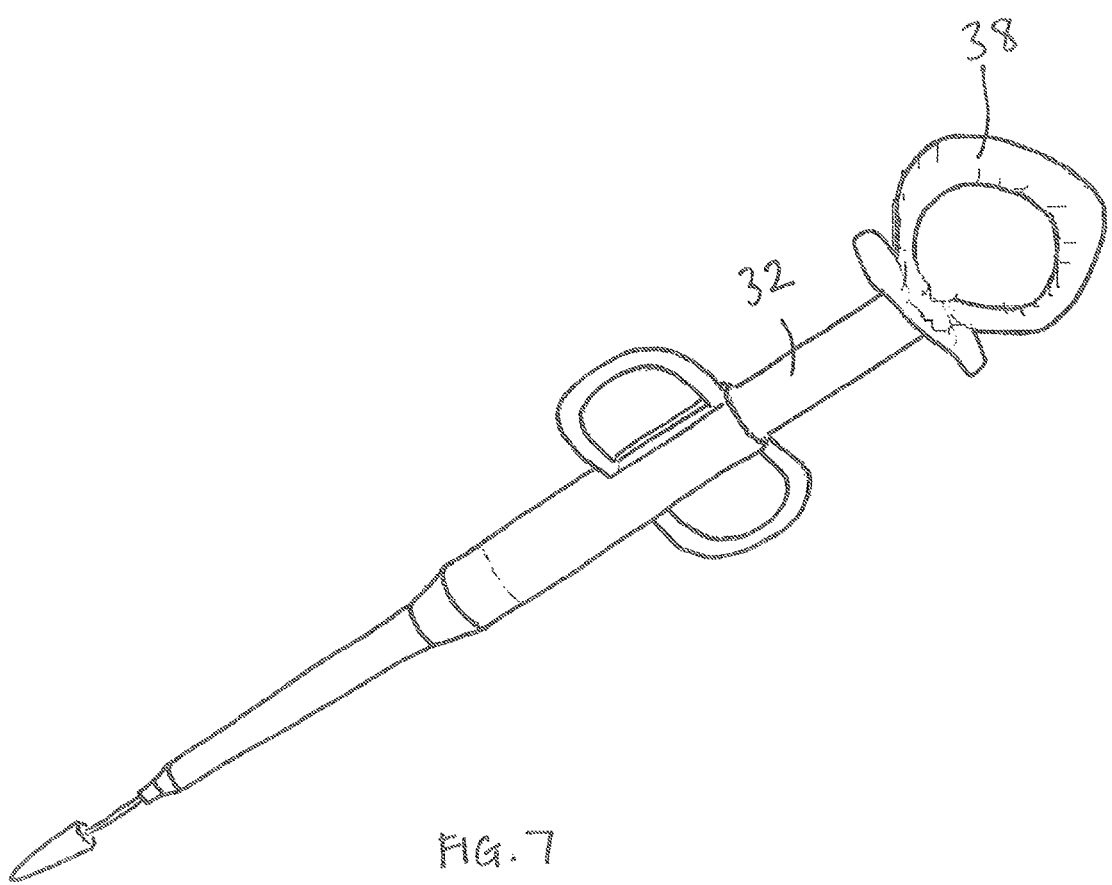
FIG. 7 shows a further embodiment of a cleaning apparatus with a ring-type handle.

In a further embodiment of the invention, illustrated in FIG. 7, the plunger 32 mounts a ring handle 38. This feature enables a user to withdraw the plunger 32 using only one finger and means the device can be operated using only one hand.

In any of the aforementioned embodiments of the invention, the brush 5 may include bristles or other projections to aid cleaning of the valve. The brush 5 may include "fin-type" projections 39 such as those shown extending radially from the core 40 of the brush 5 in FIG. 8. The projections 39 are easier to clean and harder wearing than bristles. They are made of rubber and are simple and inexpensive to manufacture.

The apparatus of the invention enables a user to efficiently clean a tracheo-oesophageal valve using a simultaneous fluid flush and rotating brush. This one step cleaning routine is much easier for a person to carry out and leads to more efficient cleaning, hence prolonging the life of the valve.

The invention claimed is:

1. A tracheo-oesophageal valve cleaning apparatus comprising:
    a fluid dispenser with a fluid reservoir containing fluid and an outlet;
    a cleaning element mounted proximal to the outlet; and
    a drive mechanism including an element mounted axially within the fluid dispenser, wherein axial movement of the element of the drive mechanism toward the outlet causes both rotation of cleaning element and fluid to be dispensed from the outlet.

2. The apparatus as claimed in claim 1 wherein the cleaning element includes radially extending projections.

3. The apparatus claimed in claim 2 wherein the radially extending projections include a plurality of substantially flexible elements.

4. The apparatus claimed in claim 3 wherein the substantially flexible elements are bristles.

5. The apparatus claimed in claim 2 wherein the radially extending projections include a plurality of substantially rigid elements.

6. The apparatus claimed in claim 2 wherein the radially extending projections extend in the axial direction of the cleaning element.

7. The apparatus claimed in claim 6 wherein at least one element protruding from the plunger locates in a substantially helical groove extending along the length of the outer surface of the rod.

8. The apparatus claimed in claim 6 wherein the plunger is slidable axially within the fluid dispenser.

9. The apparatus claimed in claim 6 wherein axial movement of the plunger causes the rod to rotate.

10. The apparatus claimed claim 6 wherein the cleaning element is mounted on the rod.

11. The apparatus claimed in claim 10 wherein the shaft is detachable from the rod.

12. The apparatus claimed in claim 6 wherein the cleaning element is mounted on the rod by means of a shaft extending between the rod and the cleaning element.

13. The apparatus claimed in claim 1 wherein the drive mechanism includes a rod and a substantially hollow plunger, the rod being mounted for rotational movement and against axial movement within the fluid dispenser.

14. The apparatus claimed in claim 13 wherein at least one element protruding from the rod locates in a substantially helical groove extending along the length of the inner surface of the hollow plunger.

15. The apparatus claimed in claim 1 wherein the cleaning element is detachable from the apparatus.

16. The apparatus claimed in claim 15 wherein the cleaning element is detachable from the shaft.

17. The apparatus claimed in claim 1 further including a lip on the outside of the fluid dispenser proximal to the outlet, the lip having a larger diameter than the cleaning element.

18. The apparatus claimed in claim 1 wherein the fluid dispenser is tapered proximal to the outlet.

19. A tracheo-oesophageal valve cleaning apparatus comprising:
    a fluid dispenser with a fluid reservoir and an outlet;
    a cleaning element mounted proximal to the outlet; and
    a drive mechanism including an element mounted axially within the fluid dispenser, wherein axial movement of the element of the drive mechanism toward the outlet causes rotation of cleaning element and is adapted to cause fluid contained within the fluid reservoir to be dispensed from the outlet, and wherein axial movement of the element of the drive mechanism away from the outlet causes rotation of cleaning element and is adapted to draw fluid into the fluid reservoir.

\* \* \* \* \*